United States Patent [19]
Gallant et al.

[11] Patent Number: 5,238,001
[45] Date of Patent: Aug. 24, 1993

[54] AMBULATORY PATIENT MONITORING SYSTEM HAVING MULTIPLE MONITORING UNITS AND OPTICAL COMMUNICATIONS THEREBETWEEN

[75] Inventors: Stuart L. Gallant, Owings Mills; Paul R. Caron, Laurel; Walter E. Palmer, Catonsville, all of Md.

[73] Assignee: Stuart Medical Inc., Owings Mills, Md.

[21] Appl. No.: 790,500

[22] Filed: Nov. 12, 1991

[51] Int. Cl.$^5$ ................................................ A61B 5/03
[52] U.S. Cl. ..................................... 128/700; 128/908
[58] Field of Search ............... 128/670, 671, 700, 908; 364/413.02

[56] References Cited

U.S. PATENT DOCUMENTS

| | | | |
|---|---|---|---|
| 3,905,355 | 9/1975 | Brudny | 128/908 |
| 3,910,257 | 10/1975 | Fletcher et al. | 128/670 |
| 4,053,951 | 10/1977 | Hudspeth et al. | 128/671 |
| 4,705,048 | 11/1987 | Pfohl | 128/908 |
| 4,889,132 | 12/1989 | Hutcheson et al. | |
| 4,909,260 | 3/1990 | Salem | 128/671 |
| 4,936,309 | 6/1990 | Cooper | 128/671 |
| 5,036,856 | 8/1991 | Thornton | 128/670 |

FOREIGN PATENT DOCUMENTS

| | | | |
|---|---|---|---|
| 0047869 | 3/1982 | European Pat. Off. | 128/700 |
| 445809 | 9/1991 | Fed. Rep. of Germany . | |
| 89/10002 | 4/1989 | PCT Int'l Appl. | |
| 89/05116 | 6/1989 | PCT Int'l Appl. | |
| 2054861 | 2/1981 | United Kingdom . | |

Primary Examiner—William E. Kamm
Attorney, Agent, or Firm—Morton J. Rosenberg; David I. Klein

[57] ABSTRACT

An ambulatory patient monitoring system (100) is provided for measuring and storing predetermined diagnostic parameters of a patient. The monitoring system includes a personal type computer (120) which may be selectively coupled to the portable portion (102) of system (100). Portable portion (102) may include one or more monitoring modules, such as ECG monitoring unit (110) and blood pressure monitoring unit (210). When ECG monitoring unit (110) and blood pressure monitoring unit (210) are disposed in side-by-side relationship and with respective optical interfaces (50, 254) in optical alignment, the two units operate in concert. ECG monitoring unit (110) supplies an R-wave gating signal to blood pressure monitoring unit (210) for establishing a window in which the receipt of a Korotkoff sound is expected. Additionally, the ECG unit (110) may trigger the blood pressure unit (210) to take a reading responsive to unit (110) identifying a predetermined abnormality in the ECG signal. Alternately, ECG monitoring unit (110) and blood pressure monitoring unit (210) may be used independently of one another as separate monitoring devices.

24 Claims, 10 Drawing Sheets

AMBULATORY PATIENT MONITORING SYSTEM HAVING MULTIPLE MONITORING UNITS AND OPTICAL COMMUNICATIONS THEREBETWEEN

BACKGROUND OF THE INVENTION

1. Field of the Invention

This invention directs itself to ambulatory monitoring systems for measuring and storing diagnostic parameters. In particular, this invention directs itself to a modular monitoring system, wherein modular monitoring units can be used either independently of one another, or utilized together with at least one module communicating to another through an optical interface. More in particular, this invention directs itself to a system wherein the patient's ECG waveform is monitored and analyzed to identify particular abnormalities, both the ECG waveform and analysis data being stored in a non-volatile memory. Further, this system is directed to a blood pressure monitoring module for taking measurements responsive to a selectively variable repetition rate, selectively actuated for predetermined time intervals, and at times triggered by the ECG monitoring unit, when both are being utilized. More in particular, this invention pertains to an ambulatory monitoring system wherein each of the monitoring unit modules includes a serial interface for coupling with a personal-type computer to allow the physician to program predetermined parameters, observe measurements in real time, and download measurement data stored in the memory of each of the modules. Further, this invention directs itself to ambulatory monitoring units having means for conserving power to enable the units to operate for over twenty-four hours on battery power. Such power conserving means may take the form of a system is vary the operational speed of the monitoring unit's microprocessor, or alternately shutting down the operation of the unit's microprocessor for predetermined periods of time.

PRIOR ART

Ambulatory monitoring systems are well known in the art.

Some prior art systems, such as that disclosed in U.S. Pat. Nos. 4,211,238; 4,216,779; and, 4,519,398 are directed to ambulatory monitoring systems for both blood pressure and a patient's ECG. In such systems the ECG signal is continuously monitored and stored in a memory or on a magnetic tape. The blood pressure measurement may be made at particular time intervals, with only a provision for manually initiating a measurement at intermediate times. Such blood pressure measurements are stored with the continuous ECG signal, however, there is no provision for the ECG unit triggering a blood pressure measurement.

In other prior systems, such as that disclosed in U.S. Pat. No. 4,566,463 automatic blood pressure monitoring systems are disclosed which are capable of operating responsive to heartbeat abnormalities. While such systems attempt to detect arrhythmias and generate a control signal for initiating the blood pressure measurement, such systems utilize pressure pulse from the blood pressure cuff as the means to detect arrythmias. Further, these systems are not of modular construction wherein the communication between modules is devoid of cabling, and the problems associated therewith. Still further, such systems lack means for conserving power, which is essential in portable long-term monitoring systems.

SUMMARY OF THE INVENTION

An ambulatory patient monitoring system is provided for measuring and storing predetermined diagnostic parameters of a patient. The ambulatory patient monitoring system includes a first monitoring unit for independently measuring and storing a predetermined first diagnostic parameter of a first patient responsive to a first control algorithm. The first monitoring unit includes a first optical interface circuit for digital communication. The first monitoring unit further includes a first memory circuit for storing the first diagnostic parameters therein. The ambulatory patient monitoring system further includes at least a second monitoring unit for measuring a predetermined second diagnostic characteristic responsive to a first control signal, and storing the second diagnostic parameter responsive to a second control algorithm. The first control signal is generated at a selectively variable repetition rate, selectively actuated for predetermined time intervals. The second monitoring unit includes a second optical interface circuit for digital communication with at least the first monitoring unit. The second monitoring unit is (1) independently operable for measuring the second diagnostic characteristic of a second patient, the second diagnostic characteristic being different than the first diagnostic characteristic, and (2) positionable in optical alignment with the first monitoring unit for measuring the second diagnostic characteristics of a first patient responsive to both the first control signal and a second control signal. The second control signal being generated by the first monitoring unit and transmitted by the first optical interface circuit to the second optical interface circuit. The second monitoring unit also includes a second memory circuit for storing the second diagnostic characteristics therein. The ambulatory patient monitoring system further includes a computing system selectively coupleable to both the first and second monitoring units for transferring data therebetween and selectively displaying the first and second diagnostic characteristics.

DESCRIPTION OF THE PREFERRED EMBODIMENTS

Figure 1:
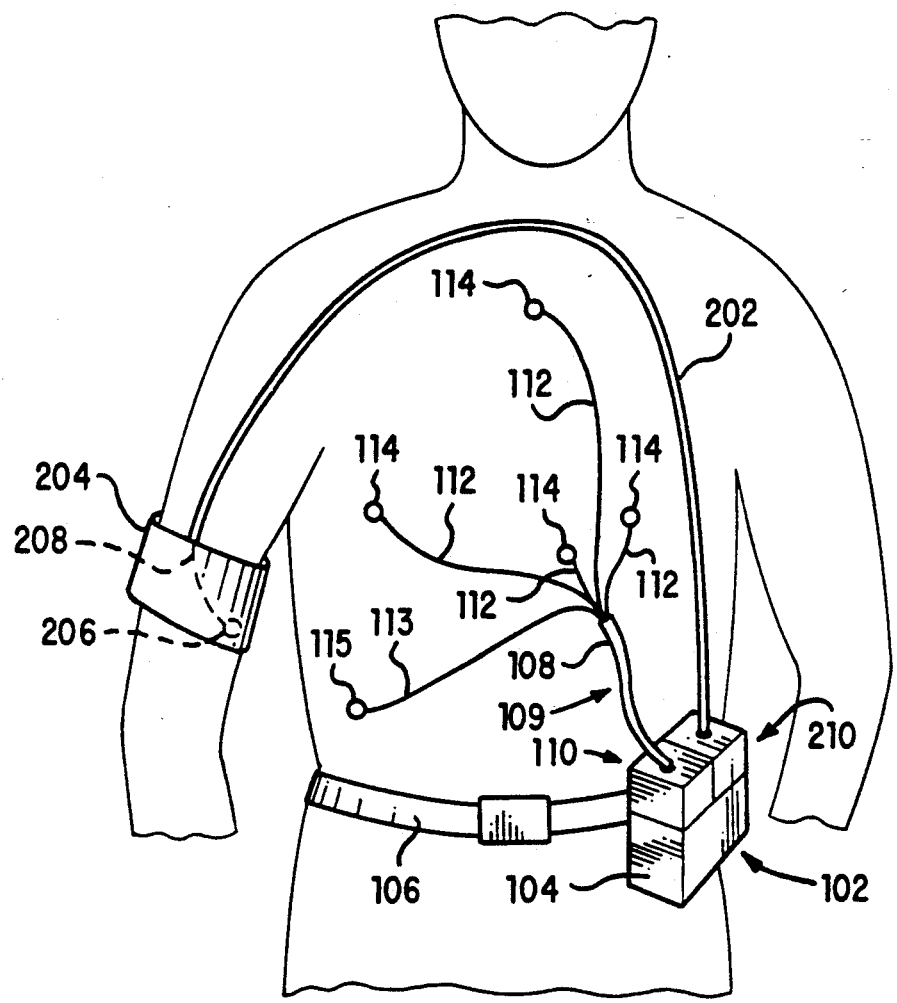
FIG. 1 is a diagram showing the ambulatory monitoring system of the present invention in use.

Referring to the Figures, there is shown ambulatory patient monitoring system 100 for measuring and storing predetermined diagnostic parameters of a patient. As will be seen in following paragraphs, ambulatory monitoring system 100 is directed to the concept of providing simultaneous ambulatory measurements of multiple diagnostic parameters, such as the electrocardiogram, blood pressure, oxygen saturation, temperature, and respiratory function, while still maintaining the capability of utilizing the measuring devices for each of the diagnostic parameters independently, on different individual patients. Although not restricted to the simultaneous measurements of the electrocardiogram and blood pressure, system 100 is particularly adapted to provide event triggered blood pressure measurements, the programmed blood pressure measurement protocol being interrupted in response to the detection of a particular ECG abnormality identified by the ECG monitoring unit 110. Additionally, the blood pressure monitoring unit 210 is further enhanced through the use of an R-wave gating signal, for use in the auscultatory method of blood pressure measurement transmitted from the ECG unit 110 to the blood pressure monitoring unit 210, the blood pressure unit 210 using the gating signal to establish a window for detecting of Korotkoff sounds (K sounds), thereby reducing the likelihood of detecting transient noise, motion artifacts, or the like as valid K sounds. Further, unit 210 is capable of measuring blood pressure in an oscillometric mode, using pressure pulsations in the cuff to establish the systolic and diastolic levels. The oscillometric method can be carried out substantially simultaneously, with both sets of measurements stored for subsequent comparison, however, there is currently no clinical need for both sets of data. Therefore, unit 210 switches to the oscillometric method when K sounds cannot be detected, acting as a fail safe. If the cuff pressure drops below a predetermined value and K sounds have not yet been detected, the cuff is reinflated and the deflation process repeated using the oscillometric method.

Ambulatory monitoring system 100 is modular in construction to provide at least three monitoring systems in one, and having the capacity to greatly exceed that number. In the configuration shown in FIG. 1, the portable portion 102 of system 100 provides for the simultaneous and coordinated measurement of both ECG and blood pressure parameters, functioning as a single instrument. Additionally, each of the monitoring units 110, 210 may be used individually, each unit being useable on a different patient. Hence, system 100 can be configured as three different instruments, two of which being operable simultaneously.

In the exemplary configuration shown in the Figures, the ECG monitoring unit 110 functions as the master unit, with the blood pressure unit 210 defining a slave unit. As a slave unit, and in addition to making measurements in accordance with a programmed protocol, the blood pressure unit is responsive to predetermined events identified by the master ECG monitoring unit 110 for initiating a blood pressure measurement. In addition to the ECG and blood pressure monitoring units, system 100 may incorporate other modular ambulatory monitoring units for use with either or both of the ECG and blood pressure units, such as for monitoring oxygen saturation, temperature, electroencephalograph signals, one or more respiratory functions, and myoelectric potentials from particular portions of the patient's body. Each of these modules may be utilized independently, or placed in various combinations to form a monitoring instrument tailored to suit the diagnostic requirements for a particular patient. For instance, an oxygen saturation measuring module could be used in combination with both units 110 and 210, or used with either one, alone. Such an oxygen saturation measurement module could function as a master unit, triggering blood pressure measurements, or as a slave, being triggered by the ECG unit 110. Further, system 100 may include a telemetric module, for transmitting data measurements, either in real time, or downloaded from a respective module's memory, for transmission to a remote receiver through an optical or radiofrequency data link.

Referring now to FIG. 1, there is shown the portable portion 102 of ambulatory monitoring system 100 as might be worn by a patient. The ECG monitoring unit 110 and the blood pressure monitoring unit 210 are disposed in side-by-side relationship within a carrying pouch 104, and releasably secured to the patient by means of a belt or strap 106. The exact form or means for releasably securing the portable portion 102 of system 100 is not important to the inventive concept, and may be accomplished by any of a number of harness or strap arrangements, well known in the art. It should be noted that units 110 and 210 need not be disposed in abutting relationship, as it is only necessary that their respective optical communication interfaces be aligned, one with respect to the other. A plurality of ECG electrodes 114, each having a respective lead 112 of a multiple lead cable 108 defining ECG lead pairs, are par of an ECG electrode assembly 109, coupled to the ECG monitoring unit 110. Electrode assembly 109 further includes a reference electrode 115 coupled to a lead 113. ECG electrodes 114 and 115 may be any of a wide variety of disposable or reusable electrodes, well known in the art.

The blood pressure monitoring unit 210 includes an inflatable cuff 204 which carries an audio transducer 206, positioned adjacent the patient's arm, for converting the K sounds to electrical signals transmitted to monitoring unit 210 through an electrical cable 208. The cuff 204 is inflated and deflated through a hose 202 coupled to a fluid pump or compressed fluid supply and a bleed valve. The transducer cable 208 may be integrated into the hose 202, wherein cable 208 is coupled to an exterior surface of hose 202, extends through the fluid carrying lumen, or through a separate lumen formed therein.

Figure 2:
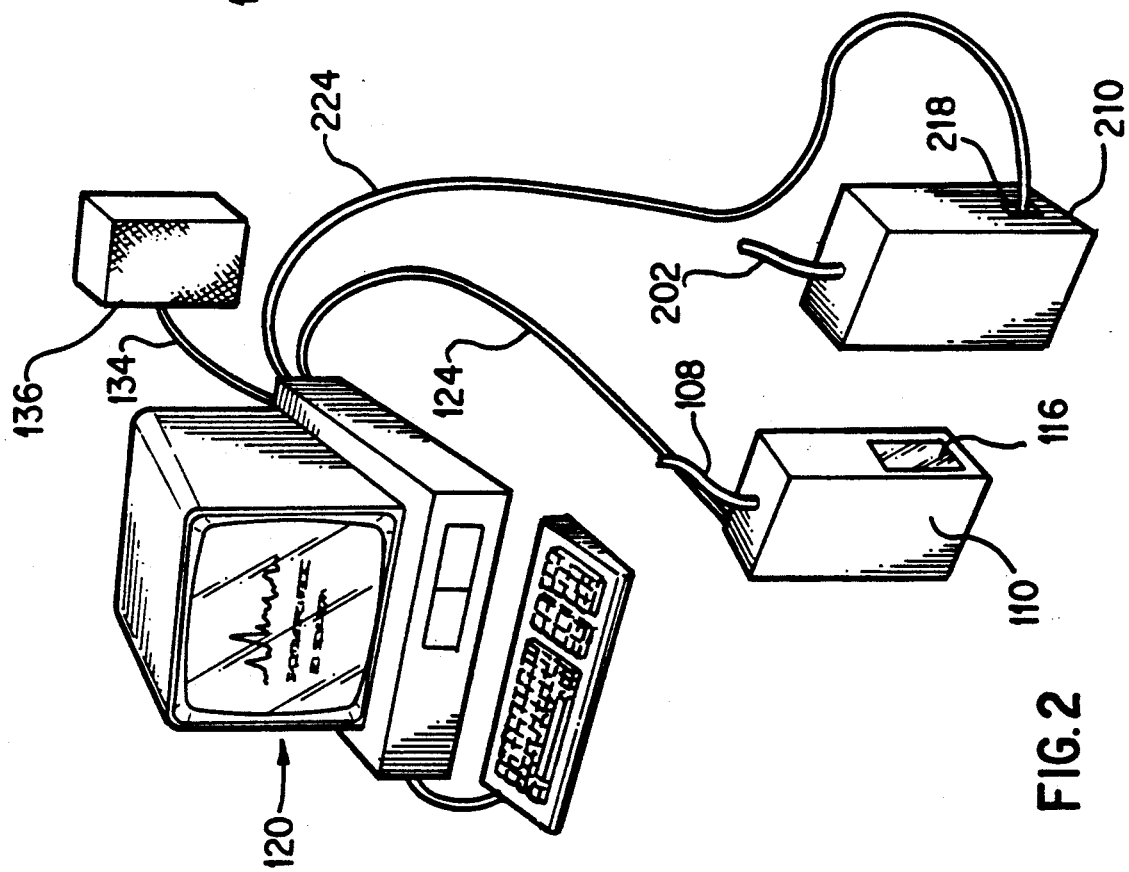
FIG. 2 is a perspective view of the ambulatory monitoring system.

Referring now to FIG. 2, there is shown ambulatory patient monitoring system 100 wherein a personal-type computer 120 is coupled to respective diagnostic parameter measuring units 110, 210, by means of optically isolated serial data links 124, 224. Bidirectional communication between the monitoring units 110, 210 and the personal-type computer 120 is provided through respective serial interfaces 48, 252 (shown in FIGS. 4 and 9) which are coupled to respective serial ports of computer 120 through respective connectors 118, 218 and serial data cables 124, 224. The physician utilizes the personal-type computer 120 to enter particular patient information, which is relevant to identifying that patient and the data collected therefrom, as well as enter particular measurement protocols, operating parameters, and event triggering data, to be more fully described in following paragraphs. Thus, the computer 120 allows the physician to program particular functions of the monitoring units 110, 210 for tailoring the diagnostic measurements to a particular patient.

The computer 120 further serves as a means for retrieving data from the respective monitoring units 110, 210. Each of units 110, 210 are provided with sufficient memory for storing the diagnostic parameters measured over at least a twenty-four hour period. Thus, all of the measurement data stored within a respective measuring unit 110, 210 can be downloaded to the main memory and mass storage systems of computer 120 through the serial data connections selectively established therebetween. Additionally, the measurement data can be transmitted to computer 120 in real time, as the measurements are being taken. In this real time data mode, the measurements can be displayed on the computer's monitor, that is, both the ECG waveforms, heart rate and blood pressure measurements can simultaneously be displayed. Additionally, the K sounds can be displayed and converted back to an audio signal for dynamically checking the blood pressure measurement data, further signal analysis and facilitating blood pressure measurement algorithm development. Computer 120 includes a digital to analog converter coupled to a speaker 136 through an audio cable 134, for playing back the K sounds while the cuff pressure measurements are displayed on the computer's monitor.

Subsequent to the stored data being downloaded, the physician can display for any time period, the ECG waveform, the heart rate, as well as display the number and time of day of the occurrence of abnormal conditions. Such abnormal conditions as arrhythmias, absence of particular ECG waveform components, and pacemaker malfunctions are separately identified and classified. Arrhythmias are further identified and classified as to type, such as ventricular tachycardia, paroxysmal supraventricular tachycardia, bradycardia, dropped beats or pauses, couplets, runs, for example. Of particular importance is the fact that ECG monitoring unit identifies these abnormal conditions as they occur, and can be programmed to trigger a concurrent blood pressure measurement concurrently therewith.

Figure 3:
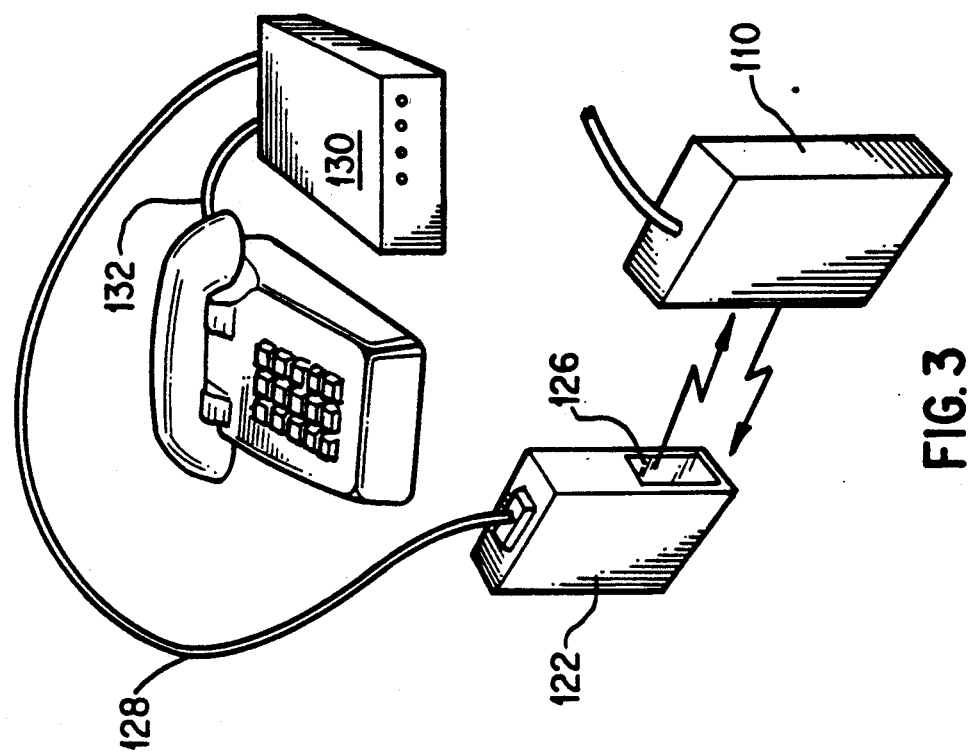
FIG. 3 is a perspective view of an alternate embodiment for the present invention.

Referring now to FIG. 3, there is shown an advantage of the optical interface 50, 254 for units 110, 210, respectively, in combination with the real time mode of the units. The patient may be provided with a modem 130 and an optical interface unit 122, coupled to modem 130 by means of a serial data cable 128 for communicating with the ECG monitoring unit 110. ECG unit 110 is being described with respect to FIG. 3 for exemplary purposes, it should be understood that blood pressure monitoring unit 210, or any other module of system 100, can be substituted interchangeably for unit 110, as this portion of the system operation applies equally to any of the monitoring units.

Optical interface unit 122 includes an optically transmissive window 126, which complements the window 116 of the monitoring unit 110, and is provided with similar circuitry to permit optically isolated communication through the telephone line 132, to the physician's personal-type computer 120, or some other computer system or digital equipment. In this fashion the physician can monitor the patient's ECG waveform remotely, or alternately download the data stored within the memory of the ECG monitoring unit 110 for monitoring the data previously obtained.

Figure 4:
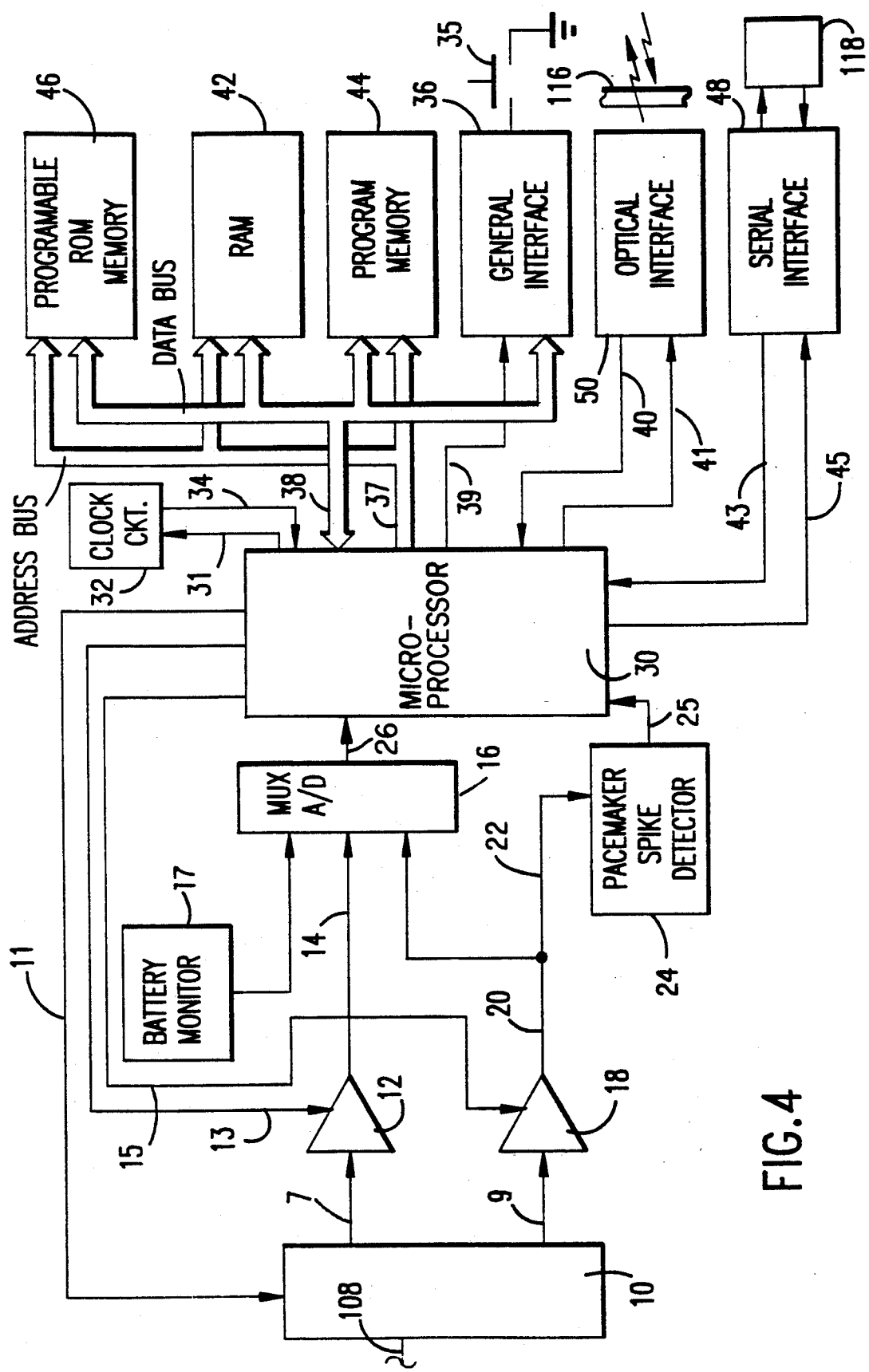
FIG. 4 is a block diagram of the ECG monitoring unit.

Turning now to FIG. 4, there is shown a block diagram for the ECG monitoring unit 110. The ECG electrode cable 108 carries signals from two pairs of electrodes 114, defining two ECG channels. The leads representing these two ECG channels are carried by the cable 108 and are coupled to an impedance switching network 10. Impedance switching network defines a digitally controlled switch capable of injecting a small test current back through the leads to the patient. This test current establishes a voltage across a respective pair of leads which is used to measure the impedance across the electrodes, thereby allowing the physician to insure proper electrode coupling with the patient. The impedance checking function carried out through the switch network 10 is controlled through the coupling line 11 which couples switch network 10 to microprocessor 30. The ECG signal amplification circuits, analog-to-digital converter, and microprocessor are utilized in this impedance measurement. Thus, the electrical signals conducted from the electrodes of the respective channels, either the substantially constant voltage of the impedance measurement or the ECG waveform signals, are coupled to respective signal conditioning circuits 12, 18 by means of respective coupling lines 7, 9.

Figure 5:
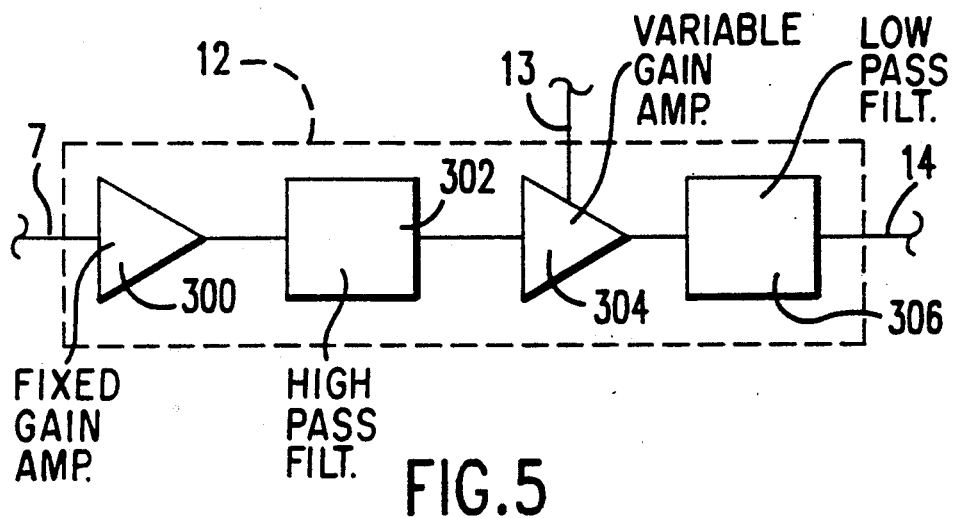
FIG. 5 is a block diagram of the ECG analog signal conditioning circuit.

As shown in FIG. 5, the signal conditioning circuit 12 comprises a fixed gain amplifier 300 having an input coupled to the coupling line 7, and an output coupled to a high pass filter circuit 302. High pass filter circuit 302 has a lower cut-off frequency approximating 0.05 hertz, and may be constructed as either an active or passive filter circuit, however, an active filter circuit is preferred. The output of high pass filter 302 is coupled to the input of a variable gain amplifier stage 304. Variable gain amplifier stage 304 is digitally programmable, having a gain control digital line 13 coupled to microprocessor 30. The variable gain of amplifier 304 stage may be adjustable within a range of 0.5–21, and preferably within a range of 3 to 12.5. Variable gain amplifier stage 304 may further include a fixed gain amplifier in combination therewith. The output of variable gain amplifying stage 304 is coupled to a low pass filter 306, having a frequency cut-off of approximately 40 hertz.

The gain of variable gain amplifier stage 304 is adjusted by microprocessor 30 by sampling the ECG signals with the gain set at a minimum value. If the peak amplitude of the detected R-wave is less than a predetermined value, the gain is increased by an incremental value. If at this increased gain step the R-wave amplitude is less than a second predetermined value, the gain is advanced another step, otherwise it will remain. Although three incremental levels of gain have proved satisfactory, obviously, more or less increments of gain could be employed without departing from the spirit and scope of the invention.

Since the second ECG channel signal conditioning circuit 18 is identical to that of circuit 12, such has not been shown. The variable gain portion of the signal conditioning circuit 18 is controlled through a digital line 15 coupled to microprocessor 30, as shown in FIG. 1, to provide independent and variable gain for that respective channel. The output 14, 20 of each of the signal conditioning circuits 12 and 18 are respectively coupled to an analog-to-digital multiplexing converter 16 by means of the respective coupling lines 14 and 20. In addition to the respective output lines 14, 20 of the signal conditioning circuits 12, 18, the output of a battery monitoring circuit 17 is coupled to one input of the multiplexing A-to-D converter 16 for providing battery condition data to microprocessor 30. When microprocessor 30 detects the low battery signal, it stores the alarm condition and the time of day that it occurred, which is recovered when the physician down loads the memory. An alarm indication could be triggered in response to a low battery condition to alert the patient, but the consequences of not doing so is simply to repeat the test, and therefore provides little justification for inclusion of the feature. Multiplexing A-to-D converter 16 sequentially converts the analog signals on each of the input lines to a multi-bit digital representation thereof, for communication to microprocessor 30 through the coupled line 26. One multiplexing analog-to-digital converter successfully utilized in system 100 is a 12-bit device having the designation TLC1540, manufactured by Texas Instruments, Inc. of Dallas, Tex.

Figure 6:
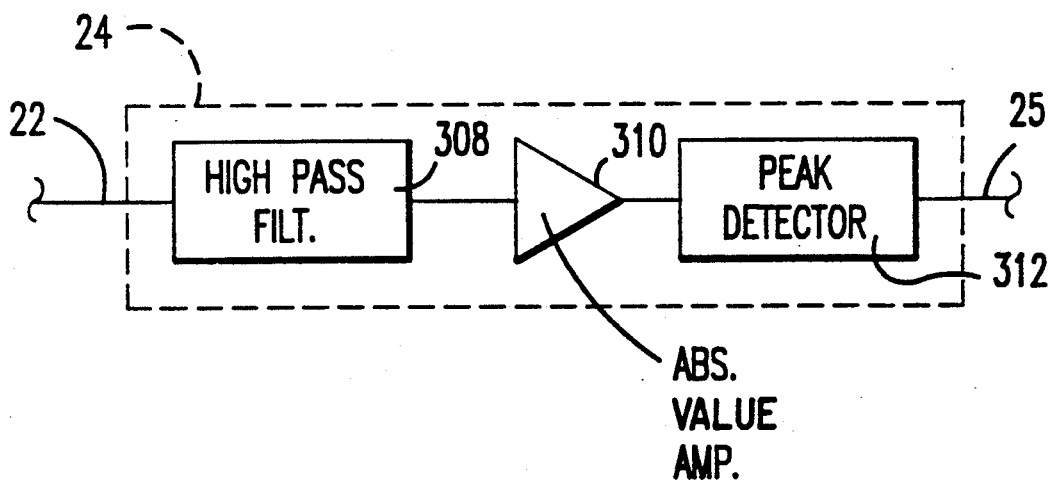
FIG. 6 is a block diagram of the pacemaker pacing spike detector.

The ECG monitoring unit 110 includes a pacemaker spike detector circuit 24 having an input coupled to the output line 20 of the channel 2 signal conditioning circuit 18. As shown in FIG. 6, the pacemaker spike detector circuit 24 includes a high pass filter circuit 308 having an input coupled to line 22. High pass filter 308 is provided with a frequency cutoff at 20 Hertz to remove the ECG signal and any muscle artifacts which might be present in the signal. The output of high pass filter 308 is coupled to an absolute value amplifier 310. An absolute value amplifier is utilized because the pacemaker spike may be either a positive or negative going pulse, which otherwise would require separate amplification and detection stages, the outputs of which would then have to be combined. Absolute amplifier 310 has a gain value approximating 500 for amplifying the pacemaker spike signal to a magnitude within the range of 10 through 500 millivolts. The output of absolute value amplifier 310 is coupled top the input of a peak detector 312. Peak detector 312 establishes a threshold value which must be exceeded for a digital logic level signal to be output on line 25 for coupling with microprocessor 30. Peak detector 312 is a conventional comparator-type circuit arrangement, well known in the art, with a threshold value approximating 15 millivolts. The pulse provided to microprocessor 30 through coupling line 25 is subsequently analyzed to determine if the signal provided on line 25 is in fact a signal representing the pacemaker spike. A pacer signal from a pacemaker has a fixed pulse width, typically in a range between 0.5 and 2.0 milliseconds, the microprocessor 30 therefore disregards any signal supplied by pacemaker spike detector circuit 24 which is outside that range. Thus, data may be accumulated on the operation of a patient's pacemaker. This feature is particularly advantageous for a patient having the type of pacemaker with a packing rate which is variable responsive to the patient's activity level.

Microprocessor 30 is a multipurpose processing device which performs communication and analytical functions of monitoring unit 110. In one working embodiment, microprocessor 30 is a commercially available 16-bit single chip microprocessor having a designation 68332, available from Motorola Semiconductor, Inc. of Phoenix, Ariz. The ECG data supplied through line 26 from the analog-to-digital converter 16 is monitored to determine whether the gain is properly set in the respective signal conditioning circuits 12 and 18, the microprocessor outputting control signals on respective control lines 13, 15 for selecting the appropriate gain values for input to the signal conditioning circuits 12, 18. Microprocessor 30 further performs real-time analysis of the ECG data, which along with the raw ECG data is processed through a data compression algorithm, and stored in the electrically erasable, electrically programmable read-only memory 46. Memory 46 is constructed from commercially available memory devices known as Flash memory devices, having a manufacturer's designation 28F020, available from Intel Corporation of Santa Clara, Calif. Data storage memory 46 provides 4 megabytes of non-volatile memory for storage of the ECG and analysis data within monitoring unit 110.

Figure 7:
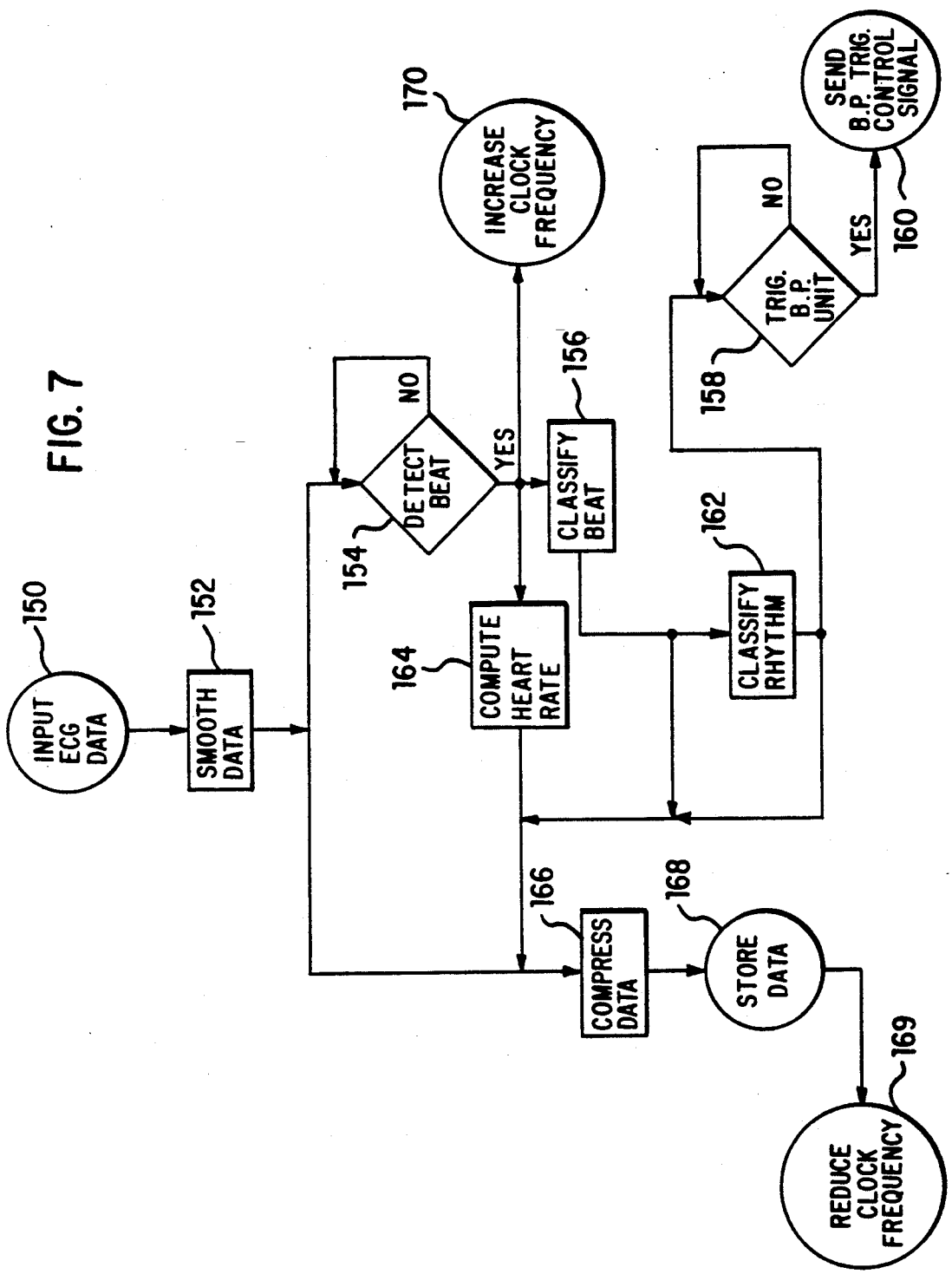
FIG. 7 is a simplified logic flow diagram of the ECG analysis.

Referring now to FIG. 7, there is shown, a simplified flow diagram of the ECG data processing steps carried out by microprocessor 30. The digitized data representing the ECG signal from either one of the two input channels (each of the channels being processed alternately) is provided from the input block 150 to the smoothing filter block 152. The smoothing filter step represented by block 152 utilizes well known techniques for enhancing the signal, with respect to noise. The smoothed data is supplied to the data compression block 166, wherein a data bit reduction procedure is carried out. The compressed data from block 166 is provided to the storage output block 168, providing the data for storage within the data storage memory 46, followed by the step of reducing the frequency of clock circuit 32, in block 167. The importance of changing the clock frequency will be described in following paragraphs.

The filtered data from block 152 is also supplied to the beat detection decision block 154. When a beat is detected, the data is transmitted from decision block 154 to the beat classification block 156 and the heart rate computation block 164. The heart rate computed in block 164 is transmitted to data compression block 166 for subsequent storage in the data storage memory 46. Classification block 156 identifies arrhythmias from the beat timing supplied from the beat detection block 165, classifying the beat into predetermined categories. The arrhythmia type identified by the beat classification block 156 is transmitted to the data compression block 166 for storage in the data storage memory 46. Additionally, the arrythmia type is transmitted to the rhythm classification block 162 so as to further distinguish reoccurring events from those of a transient nature. The output of rhythm classification block 162 is similarly transmitted to the data compression block 166 for storage in data storage memory 46. The output of the beat classification block 162 is also supplied to the blood pressure trigger detection decision block 158, and if the type of arrhythmia or rhythm identified by block 162 matches that which has been predetermined to require a simultaneous blood pressure measurement, previously entered by the physician, than the signal transmission output block 160 is enabled, for sending a trigger control signal to the blood pressure unit through the optical data link, as has previously been described.

Referring additionally to FIG. 4, microprocessor 30 is coupled to a clock circuit 32, which may be provided internal to microprocessor 30 or as an ancillary device. Clock circuit 32 provides the basic clock impulses, whose frequency determined the operational speed at which microprocessor 30 operates. The clock signals output from clock circuit 32 are supplied to microprocessor 30 through coupling line 34, as is conventionally found in microprocessor systems. However, microprocessor 30 includes an output line 32 coupled to clock circuit 32 for controlling the clock frequency supplied therefrom.

As is well known in the art, complementary metal oxide microprocessor devices consume power in direct relation to their operating speed, thus it is possible to reduce the power consumption of microprocessor 30 by maintaining a low clock frequency. This however, would have a detrimental effect on performing data compression and arrhythmia analysis in real time. To achieve the advantages of a reduced clock frequency, while obviating the disadvantage such would have on processing intensive functions, the clock speed control output 32 is utilized to adapt the clock circuit frequency to the function being performed by the microprocessor. Thus, responsive to detection of heart beats in decision block 154, the frequency of clock 32 is increased to support the real time processing of the ECG data. It should be understood that the frequency reduction step of block 169 is not reached until all of the data, raw and analysis, has been stored.

Thus, for high powered processing (significant computation), the clock circuit is operated at its highest frequency, 8 megahertz for example, and during periods, between heartbeat signals, the clock frequency may be reduced down to its lowest operating frequency, such as 32 kilohertz, or some frequency in between those limits, as a function of the type of processing which is to be performed. Use of this adaptable clock frequency saves considerable power in ECG monitoring system 110. This power saving feature is of critical importance for a portable system operating from a battery power supply, which must function continuously and reliably for over a 24-hour period. Minimization of power supply size substantially contributes to minimization of unit 110, which provides particular advantages for a device that must be worn by a patient for extended periods of time.

As previously described, microprocessor 30 provides output data which is stored in the programmable read-only memory 46, through the data bus 38 with appropriate addressing supplied through the address bus 37. Microprocessor 30 is further supported by 128-kilobytes of random access memory 42 as temporary storage for use in the data compression and arrhythmia analysis processing. The operations of microprocessor 30 are controlled by a program stored in program memory 44, coupled to the data bus 38 and address bus 37. Program memory 44 is a 256-kilobit read-only type memory. Read-only type memory 44 may be constructed of the Flash type memory devices, similar to those utilized in memory 46, thereby allowing field upgrades of the control program software ECG monitoring unit 110 utilizing the electrical erasure and programming functions of the device. In this manner, each of the memory subsystems 42, 44 and 46 are each coupled to data bus 38 and address bus 37. Also coupled to data bus 38 is a general I/O interface 36 which is selected by means of the I/O port selection control line 39, coupled to microprocessor 30. The input to general interface 36 is coupled to a momentary push-button switch 35 for coupling a reference potential thereto. Switch 35 functions as an event switch, which functions as an event marker for the ECG signal. Thus, if the patient finds himself out of breath, or lightheaded for example, he can mark the occasion utilizing the event switch. An indication that the event switch was operated will be stored along with the ECG data currently being measured. General interface 36 may comprise a commercially available 74HCT540 tri-state buffer line driver, available from Motorola Semiconductor Products, Inc. of Phoenix, Ariz.

As previously described, ECG monitoring unit 110 includes a serial interface connector 118 for coupling with an external computing device. Connector 118 is coupled to serial interface 48 by means of a respective serial input and output line, the serial interface being coupled in turn with microprocessor 30 by means of respective input and output lines 43 and 45. Serial interface 48 may be incorporated into microprocessor 30, or constructed from any one of a plurality of commercially available serial interface circuits for coupling with microprocessor 30. Similarly, the optical interface 50 is coupled to microprocessor 30 by means of respective input and output lines 40 and 41. The optical interface 50 converts electrical signals transmitted from microprocessor 30 into optical signals, preferably within the infrared bandwith of the electromagnetic spectrum, which are transmitted through the tranmsissive window 116 to a slave module, such as the blood pressure measuring unit 210. Optical signals from the slave module pass through transmissive window 116 and are received by an optical detector, such as a phototransistor, for conversion to electrical signals which are transmitted to microprocessor 30 by line 40.

Figure 8:
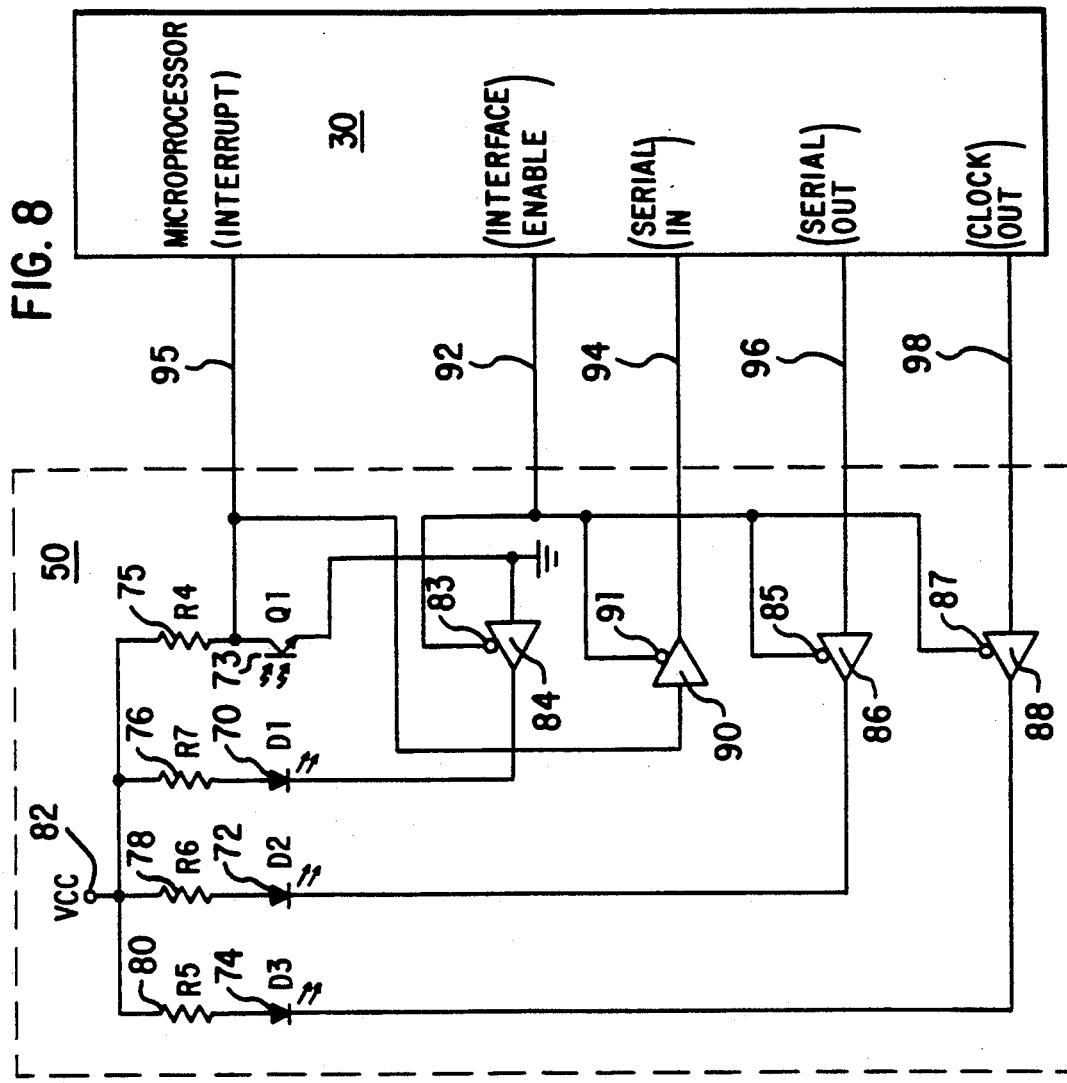
FIG. 8 is a circuit diagram of the ECG optical interface.

Referring now to FIG. 8, there is shown the optical communications interface 50 coupled to microprocessor 30. Optical interface 50 includes three light emitting diodes 70, 72 and 74, each coupled in series with a respective current-limiting resistor 76, 78 and 80. Each of resistors 76, 78 and 80 being coupled to a common power supply terminal 82 for receiving the positive power supply voltage thereon. The opposing end of light emitting diodes 70, 72 and 74 being coupled to the output of a respective tri-state buffer amplifier 84, 86 and 88. The use of tri-state buffers for driving the light emitting diodes 70, 72 and 74 is another power-saving feature incorporated into ECG monitoring unit 110.

The light emitting diodes are turned off when the interface is disabled, by means of the interface enable control line 92 coupling microprocessor 30 to each of the tri-state control inputs 83, 85 and 87 of the respective tri-state amplifiers 84, 86 and 88 coupled to light emitting diodes 70, 72 and 74. Thus, when the drives are placed in the high impedance mode, disabling the interface, no power is consumed by the light emitting diodes. This would otherwise not be the case, since the state of some of the peripheral lines, such as the clock line 98 cannot be controlled and thus, would otherwise permit the light emitting diodes to consume power.

When microprocessor 30 outputs a logic low lever signal on line 92, each of the drivers 84, 86 and 88 is enabled, turning light emitting diode 70 on, allowing transmission of serial data from line 96 through the light emitting diode 72, and transmission of the serial clock from line 98 through light emitting diode 74. Serial data is received from the slave module, such as the blood pressure monitoring unit 210, through the phototransistor 73. Phosotransistor 73 is coupled in series with a load resistor 75, which is in turn coupled to the positive power supply input terminal 82. The emitter of the phototransistor 73 is coupled to the ground reference potential for the system. The output of phototransistor 73, taken from the collector thereof, is coupled directly to microprocessor 30 on interrupt line 95.

The presence of a signal in interrupt line 95 alerts the microprocessor to the transmission of data from the slave module, in order to interrupt its current processing operation and direct appropriate resources to the receipt of the incoming data. Additionally, the output of phototransistor 73 is coupled to the input of the tri-state buffer amplifier 90 for transmission through the serial input line 94 to microprocessor 30. As with the other tri-state buffer amplifiers, amplifier 90 includes a tri-state control input 91 which is coupled to the interface enable control line 92. When the slave module initiates an optical transmission to ECG unit 110, the received signal changes the logic state of interrupt line 95 from a high to a low level, generating the interrupt signal internal the microprocessor 30. Microprocessor 30 responds by changing the logic level of the interface enable line 92 form a high to a low, illuminating light emitting diode 70 to indicate to the slave module that microprocessor 30 is ready to receive data, the data being synchronized with the serial clock signal of microprocessor 30, transmitted by light emitting diode 74. With respect to the block diagram of FIG. 4, output lines 92, 96 and 98 are represented by coupling line 41, and input lines 94 and 95 are represented by coupling line 40.

Each of units 110 and 210 are capable of using their respective optical interface to automatically detect the presence of the other respective unit. When unit 110, for instance, is turned on and completes initial self test and calibration functions, a signal is transmitted by the optical interface 50. If after a predetermined delay no response is received, ECG unit 110 operates as an independent unit, unless an interrupt signal is received on line 95 at some later time. In this manner ECG unit 110 can save power, by not transmitting an R-wave gating signal for every beat. Similarly, the blood pressure unit 210 is capable of detecting the presence of the ECG unit, for determining whether it is to function as an independent unit. However, the operational mode of unit 210 could be set at the time the measurement protocol is programmed by the physician.

Figure 9:
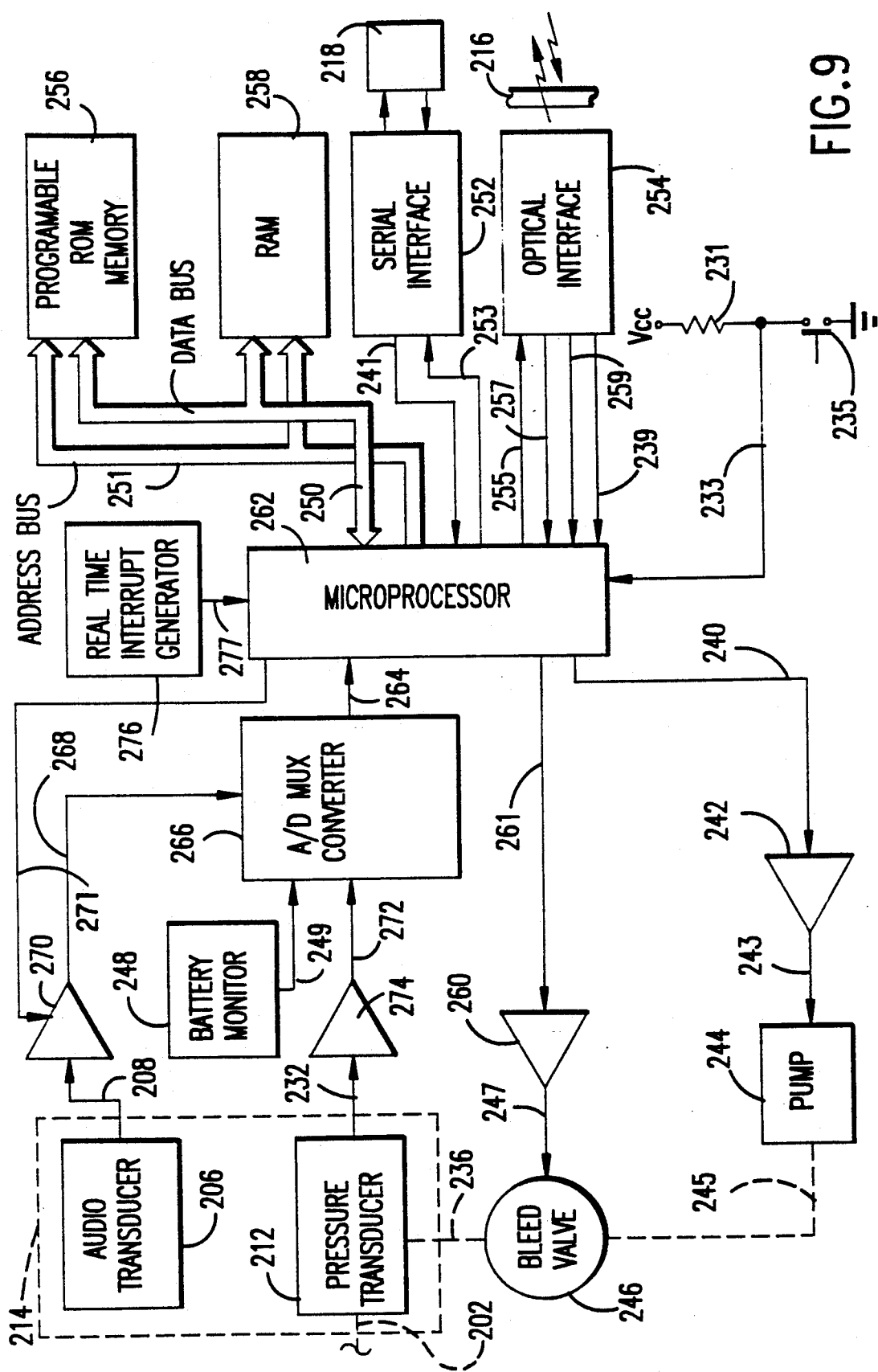
FIG. 9 is a block diagram of the blood pressure monitoring unit.

Referring not to FIG. 9, there is shown a block diagram of the blood pressure monitoring unit 210. A transducer assembly 214 includes an audio transducer 206, which may be a microphone, for converting the K sounds into electrical signals transmitted by electrical cable 208 to signal conditioning circuit 270, which performs amplification and filtering functions, to be described in following paragraphs. The output of signal conditioning circuit 270 is coupled to analog-to-digital multiplexing converter 266 through coupling line 268. Coupling line 268 represents the output of several signals from signal conditioning circuit 270, to be more fully described in following paragraphs. The digitized output of the analog-to-digital multiplexing converter 266 is supplied to microprocessor 262 through coupling line 264. Microprocessor 262 provides a control signal to signal conditioning circuit 270 by means of coupling line 271 for controlling the amplification gain thereof.

The transducer or sensor assembly 214 further includes a pressure transducer 212 for measuring the inflation pressure of cuff 204 through hose 202. The electrical output of pressure transducer 212 is coupled to amplifier 274 through coupling line 232. The output of amplifier 274 is coupled to analog-to-digital multiplexing converter 266 through coupling line 272. As in the ECG monitoring unit 110, blood pressure monitoring unit 210 includes a battery monitoring circuit 248 having an output coupled to an analog-to-digital multiplexing converter 266 through coupling line 249. Microprocessor 262 stores the alarm condition and time of day it occurred with the blood pressure data. Thus, the multiple outputs derived from the audio transducer, the output from the pressure transducer, and the output of the battery monitor are sequentially digitized and transmitted to microprocessor 262. Analog-to-digital multiplexing converter is a commercially available device, like that utilized in monitoring unit 110, previously described.

Microprocessor 262 may be an 8-bit microprocessor having internal serial interface circuitry. One such microprocessor which has been successfully utilized in this application has an identification number of 68HC811, from Motorola Semiconductor Products, Inc. of Phoenix, Ariz. Microprocessor 262 outputs a pump control signal on line 240 which is coupled to a driver amplifier 242. The output of the driver amplifier 242 is coupled to the pump 244 by means of the coupling line 243. Pump 244 pumps fluid through an output conduit 246 through bleed valve 246 and conduit 236 to pressure transducer 212, for coupling with cuff 204 through hose 202. In particular, the fluid utilized is air, although other fluids may be substituted. As an alternative, pump 244 may be replaced by an electrically actuated valve coupled to a supply of compressed fluid, which may be utilized to inflate cuff 204.

Transducer assembly 214 is utilized during the inflation step of the blood pressure measurement to determine when the patient's brachial artery has been occluded by the cuff, the pressure being over a predetermined value and there being an absence of K sounds. When the occlusion pressure is reached, pump 244 is shut down, by the change in state of the control signal output on line 240. Subsequently, a control signal is output on line 261 which is supplied to driver amplifier 260. Driver amplifier 260 provides an output on line 247 for controlling the bleed valve 246, which controls the release of fluid from cuff 204 through hose 202 on conduit 236.

The rate at which fluid pressure is bled from the cuff 204 is controlled by the outlet orifice of bleed valve 246, with the increments of pressure at which the microprocessor checks for the presence of K sounds being controlled by the length of time that the bleed valve is opened, that length of time being the time between beats. Thus, if the bleed rate were 2 millimeters of Hg per second, and the patient's heart rate was 90 beats per second, the cuff pressure would decrease approximately 1.3 mm of Hg. When the pressure is dropped, the microprocessor would check for detection of a K sound, and then proceed to open the bleed valve for the next interval between beats. Each incremental pressure value is stored in memory during the measurement procedure. As in conventional blood pressure measurements, subsequent to the first K sounds being detected, the reduction in pressure in cuff 204 continues until there is an absence of K sounds. When R-wave gating is supplied by the ECG monitoring unit 110, the microprocessor only looks at the output of peak detector 336 a predetermined delay time after the R-wave signal. The pressure at which the K sounds cease to be detected establishes the diastolic pressure.

Figure 10:
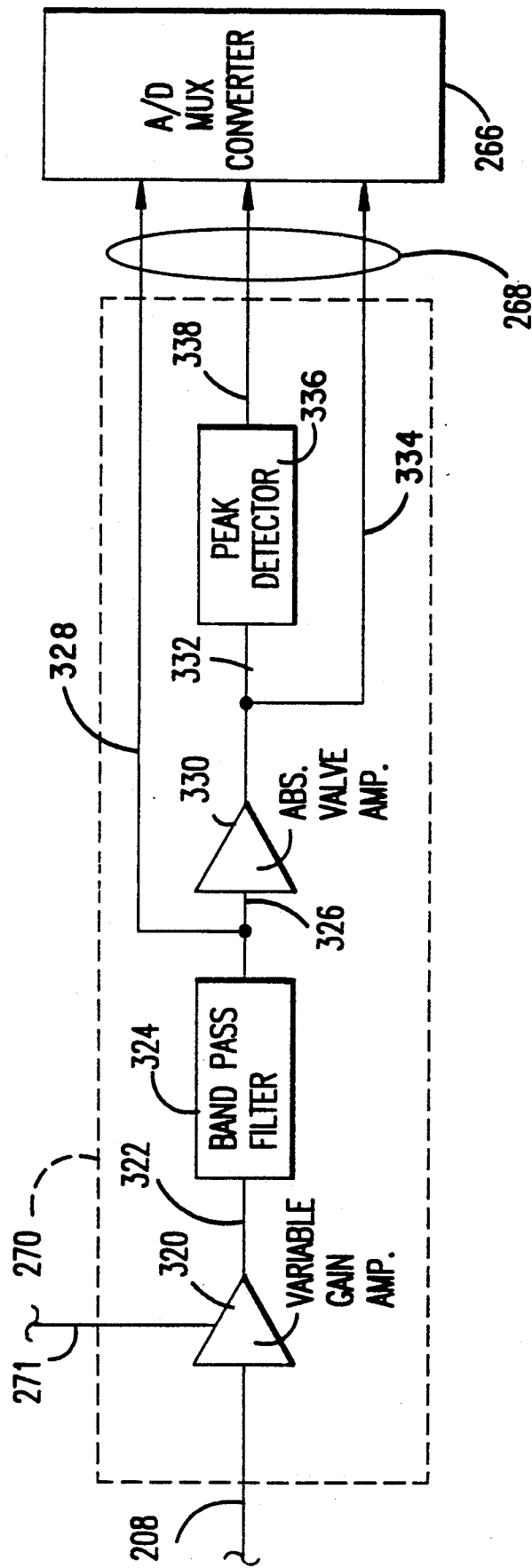
FIG. 10 is a block diagram of the K sound signal conditioning circuit.

Referring not to FIG. 10, there is shown, a block diagram of the signal conditioning circuit 270. The electrical signals from audio transducer 206 are supplied by line 208 to a variable gain amplifier stage 320. The gain of amplifier 320 is controlled by a signal from microprocessor 262 through the coupling line 271. The output of variable gain amplifier 320 is coupled to a band pass filter 324 by means of line 322. Although not important to the inventive concept, band pass filter 324 may be an active filter circuit having a center frequency approximating 23 hertz, low frequency cutoff approximating 11.5 hertz and an upper frequency cutoff approximating 34.5 hertz. The output of band pass filter 324 is coupled to one channel of analog-to-digital multiplexing converter 266 through coupling line 328, providing the K sound audio signals to microprocessor 262 for storage and subsequent analysis.

The provision for storing actual K sounds is a critically important new feature for ambulatory blood pressure monitoring units. In conventional systems the physician manually takes a patient's blood pressure while the patient is at rest, comparing the manual measurement with the ambulatory unit's measurement. Heretofore there has been no way for the physician to check the ambulatory unit's calibration while the patient is active, when there is potential for greater inaccuracy due to motion artifacts. Since the actual K sounds are stored along with the pressure data in memory, the physician can listen to the K sounds and observe the cuff pressure reading to establish his own blood pressure measurement, for comparison with which was determined by the measurement algorithm. Additionally, the stored K sounds can be input to more sophisticated analysis systems for further analysis. The stored K sounds facilitate the development of new blood pressure measurement algorithms, providing an easy method for evaluating their accuracy over a wide range of patient activity.

Additionally, the output of band pass filter 324 is supplied to absolute value amplifier 330 through coupling line 246. Absolute value amplifier 330 converts the bipolar audio signal output from filter 324 into a unipolar signal and outputs a signal representing the envelope thereof. The K sound envelope is coupled to a respective channel of analog-to-digital multiplexing converter 266 through coupling line 334. The output of absolute value amplifier 330 is also coupled to peak detector 336 by means of coupling line 3332. Peak detector 336 provides a pulse output responsive to the K sound envelope signal exceeding a predetermined threshold, thereby providing a pulse indicating detection of a K sound. The output of peak detector 336 is coupled to yet another channel of analog-to-digital multiplexing converter 266 by means of coupling line 338. Each of the signal lines 328, 334 and 338 are represented by the signal line 268 in the block diagram of FIG. 9.

Referring back to FIG. 9, there is shown, a real time interrupt generator 276 coupled to microprocessor 262 by means of the coupling line 277. Real time interrupt generator 276 forms part of a power saving subsystem of blood pressure monitoring unit 210. Blood pressure monitoring unit 210 is periodically put in a "sleep" mode wherein the microprocessor operation is stopped and the current draw is dropped to the microamp level, providing a substantial power savings. Subsequently, responsive to an output from real time interrupt generator 276 the microprocessor is "awakened" to perform housekeeping chores, such as incrementing counters and checking status of communication ports, and taking blood pressure measurements, as required.

Figure 11:
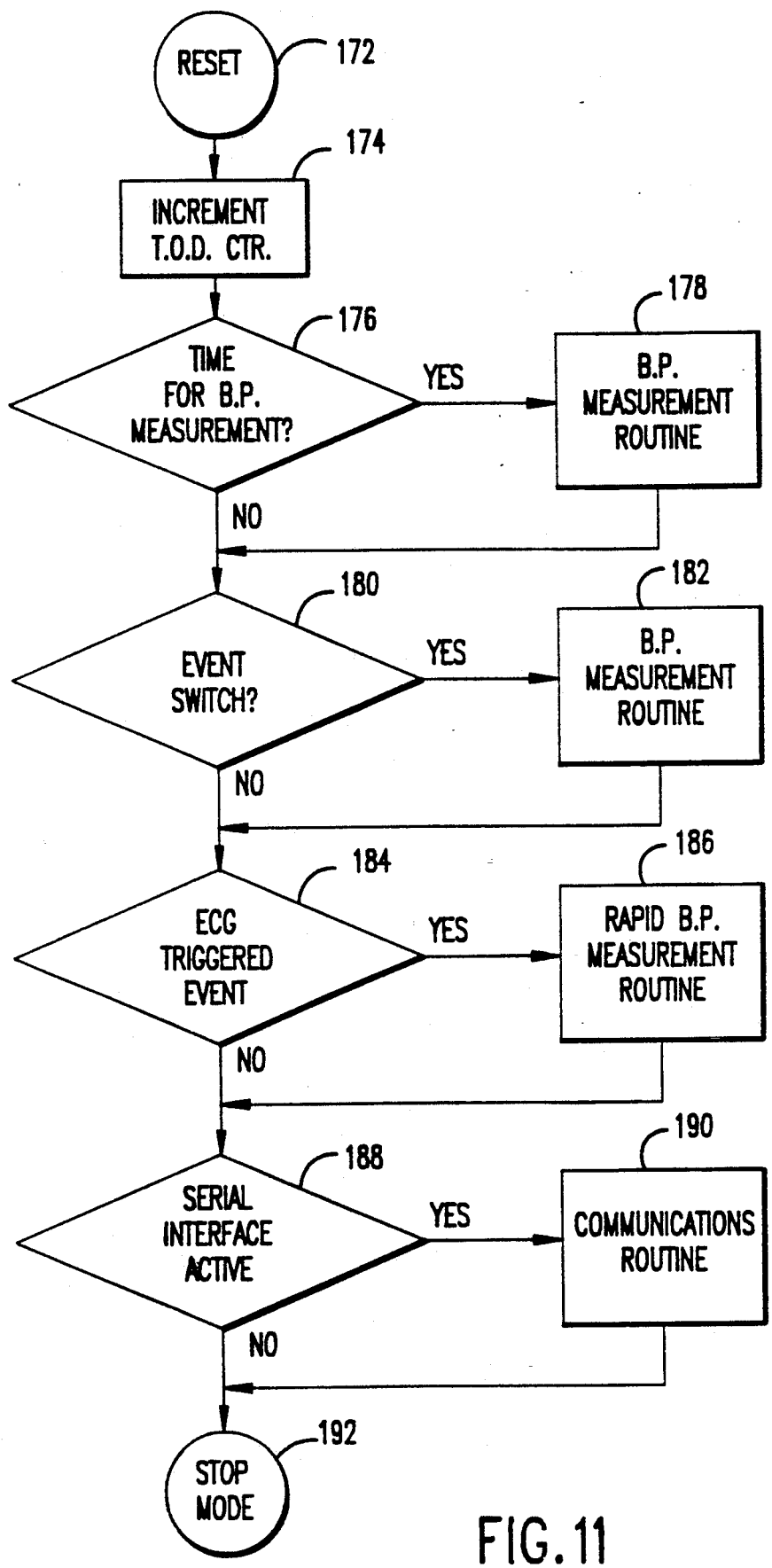
FIG. 11 is a simplified logic flow diagram for the blood pressure monitoring unit; and, FIG. 12 is a simplified logic flow diagram of the rapid blood pressure measurement method.

Referring not to FIG. 11, there is shown, a simplified flow diagram representing the cyclic operation of microprocessor 262. Responsive to an output real time interrupt generator 276 a reset of microprocessor 262 is initiated at block 172. The signal from real time interrupt generator 276 is a repetitive clock signal defining a predetermined increment of time, for example, 0.5 seconds. Thus, subsequent to initiation of the reset defined by block 172, the time of day counter is incremented in block 174. The incremented counter of block 174 provides a time of day which is compared in block 176 with a selected measurement protocol to determine if it is time for a blood pressure measurement to be taken. If a True condition results, then the microprocessor's activity is controlled by the blood pressure measurement routine indicated by block 178. The measurement protocol which can be programmed by the physician is quite versatile. In additional to setting a repetition rate for the measurements, the rate can be varied at different portions of the day. For instance, blood pressure measurements may be scheduled to be taken every 10 minutes from 7:00 to 9:00 A.M., every 30 minutes from 9:00 A.M. to 7:00 P.M., and every 60 minutes from 7:01 P.M. to 6:59 A.M.

Subsequent to the measurement routine indicated in block 178 being completed, or subsequent to the comparison step of block 176, where a Not True results, the microprocessor then tests, in block 180, whether the event switch has been operated. If the event switch has been operated then the microprocessor proceeds to perform a blood pressure measurement as indicated in block 182. If the event switch has not been operated, or subsequent to the blood pressure measurement having been made, the microprocessor checks the optical interface to determine if the ECG unit 110 is signalling that a blood pressure measurement should be taken, so as to correspond to the occurrence of some predetermine abnormality in the ECG signal. If such an event has occurred, then, as indicated in block 186, the microprocessor performs a rapid blood pressure measurement, as will be more fully described in following paragraphs. If the ECG has not triggered a blood pressure measurement, or such has been completed, the microprocessor than looks to the serial interface 252 to determine if it is active, as indicated in block 188. If the result of this test is True, then the microprocessor performs the necessary communications operations, as indicated in block 190. If the test of block 188 is Not True, or such communications is completed, the microprocessor is then put in a stop mode, as indicated by block 192, wherein its functions cease and power consumption is substantially reduced. This power saving feature is of critical importance to the design of monitoring unit 210, permitting continuous operation for greater than 24 hours with a smaller size battery power supply than would otherwise be required. Such facilitates unit 210 being constructed as a small compact unit, which is particularly advantageous for a device which must be worn by a patient for extended periods of time.

The event switch 235, shown in FIG. 9, is a momentary push-button switch coupled in series with a load resistor 231 between the positive power supply voltage, on one end of resistor 231, and the power supply reference coupled to the opposing terminal of switch 235. Coupled to the node between switch 235 and load resistor 231 there is provided an input line 233 coupled to an input terminal of microprocessor 262. By this arrangement, line 233 is held at a high logic level when switch 235 is open, and brought to a low logic level when the contacts of switch 235 are closed.

Optical interface 254, coupled to microprocessor 262, is constructed to complement that of optical interface 50 of the ECG monitoring unit 110. That is to say, that optical interface 254 is provided with a single light emitting diode for transmitting data from the blood pressure unit, and three phototransistors arranged to receive respective optical signals from each of the light emitting diodes 70, 72 and 74 of optical interface 50. The enabling signal transmitted by light emitting diode 70 is received by a respective phototransistor in optical interface 254 for transmission to microprocessor 262 through coupling line 239. Similarly, an optical signal transmitted from light emitting diode 74 of optical interface 50, through light transmissive window 216 of blood pressure monitoring unit 210 is received by a respective phototransistor for transmission of the clock signal to microprocessor 262 through line 259. The received clock signal being utilized for synchronization of the serial transmission sent to ECG monitoring unit 110 and the transmission received therefrom. Thus, the serial data transmitted from light emitting diode 72 of optical interface 50 is received by a respective phototransistor within optical interface 254 and transmitted to the serial input of microprocessor 262 through line 257. The serial data transmitted from microprocessor 262 is transmitted to optical interface 254 by line 255, wherein a light emitting diode is driven to provide an optical output transmitted through transmissive window 216 to ECG monitoring unit 110 for receipt by phototransistor 73.

A serial interface 252 is provided for communication with such devices as the personal type computer 120 shown in FIG. 1. The serial interface connected 218 provides the means for coupling serial input and output lines, through serial interface 252, to respective serial input and output ports of microprocessor 262. Serial data from microprocessor 262 is carried by line 253 to serial interface 252, and serial data therefrom is transmitted to microprocessor 262 by line 241.

Blood pressure measurements which are taken, in addition to the raw audio signals, and the K sound envelope, are all stored in programmable read-only memory 256. Programmable read-only memory 256 is an electrically erasable programmable read-only memory for providing non-volatile storage of the blood pressure measurement data. Additionally, the software required to operate microprocessor 262 is stored within programmable read-only memory 256, along with the selected measurement protocol entered by the physician through the personal type computer 120. Subsequently, the data is read from memory 256 and transmitted through serial interface 252 for display, and possible subsequent processing by personal computer 120. Electrically erasable read-only memory 256 is formed by Flash memory devices, similar to those utilized in the ECG monitoring unit 110. One such Flash memory device has the part number designation 28F020, available from Intel Corporation of Santa Clara, Calif. Programmable ROM memory 256 is coupled to microprocessor 262 through the bi-directional data bus 250 and address bus 251. Further, microprocessor 262 is coupled to 128 kilobit random access memory 258 by means of bi-directional address bus 250 and address bus 251. Random access memory 258 provides short-term storage for data processing and a unique program storage function, to be further described in following paragraphs.

Blood pressure monitoring unit 210 is provided in a very compact form, utilizing a minimum number of components, minimizing power consumption, and maximizing efficiency of those components utilized. By maintaining the program storage within the same memory subsystem as is utilized for data storage, storage density is maximized, as data may be stored beginning with those memory locations immediately following those utilized for program storage. If subsequent software upgrades enlarge the size of the program storage requirements, the data storage is just simply started at a higher address location. As long as the total remaining programmable read-only memory is sufficient for a 24-hour period of data accumulation, the overall system performance will not be affected. However, in such systems wherein the program memory is separate from the data memory, excess storage capacity must be reserved for future expansion, and future increases in storage requirements for program memory could necessitate hardware modifications to provide additional storage, even though the data memory contains excess storage capacity. This wastefulness, adding memory in one area while an excess of memory exists in another, is eliminated by storing the operating program in the same non-volatile memory as the data. However, in order to accommodate this virtual program memory storage, such eliminates the ability to selectively erase only the data storage portion of memory 256.

The solution to this latter problem is provided with the utilization of the random access memory 258. Prior to erasure of programmable read-only memory 256, the operating program for microprocessor 262 is transferred from read-only memory 256 to random access memory 258. Subsequent to the transfer of the operating program, programmable read-only memory 256 is erased, to permit use on a new patient, or to gather another 24-hour accumulation of data on the same patient. While the operating program is stored in random access memory 258 such can be modified with new measurement protocols entered by the physician through serial interface 252. Additionally, if the operating program is to be replaced, such replacement may be entered through interface 252 for storage in programmable read-only memory 256, subsequent to erasure thereof.

Figure 12:
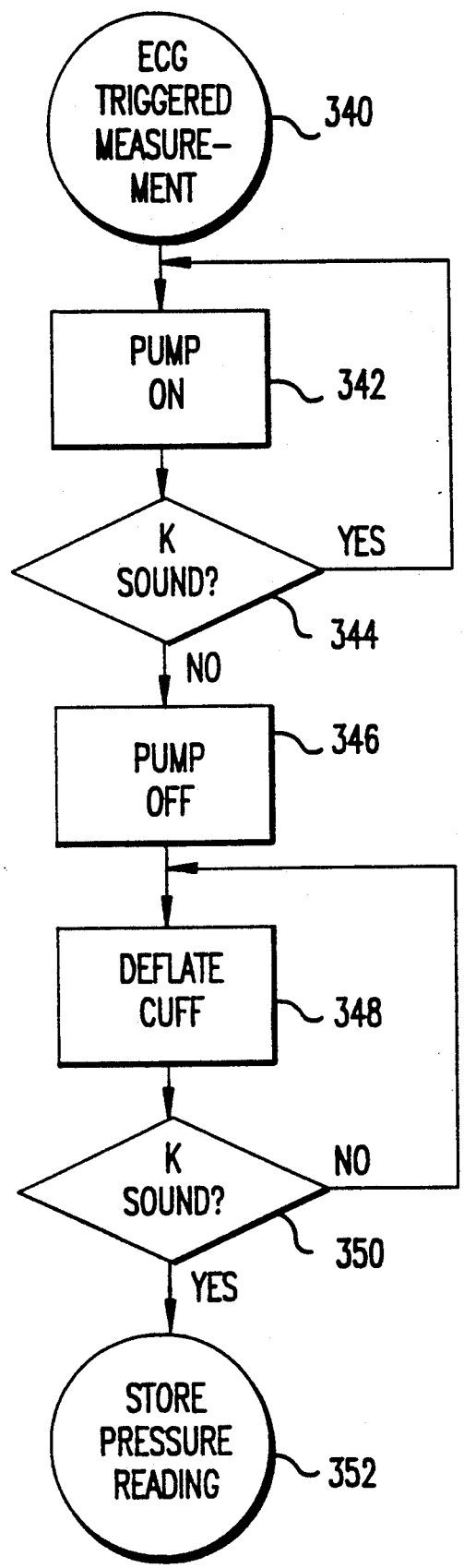

Referring not to FIG. 12, there is shown a flow diagram for the rapid blood pressure measurement selected to be utilized by the physician, responsive to particular transient abnormal conditions identified by the ECG monitoring system 110. Responsive to the ECG monitoring unit triggering a blood pressure measurement at entry block 240, the pump 244 is turned on, as indicated in block 342. Subsequent to the pump turn on, and after a predetermined delay to inflate the cuff to a predetermined pressure, microprocessor 262 tests to see if K sounds are present, as indicated in block 344. If K sounds are present, such indicates that the brachial artery is not occluded, and the inflation provided by the energization of pump 244 continues until K sounds are not longer detected. When K sounds are no longer detected, pump 244 is turned off, as indicated in block 346. Immediately thereafter, the bleed valve 246 is deflated in predetermined, relatively large steps, in the approximating range of 5.0–10.0 millimeters of Hg, indicated in block 348. At each incremental drop in cuff pressure, microprocessor 262 tests to determine if any K sounds are present, as indicated in block 350. If no K sounds are found, the cuff 204 is deflated another increment, this process continuing until K sounds are detected. When K sounds are detected the pressure reading, as indicated by an output from the pressure transducer 212, is stored in memory, as indicated in block 352. By utilizing this rapid deflation of cuff 204 in order to establish a coarse approximation of the systolic blood pressure, a clinically significant measurement is provided for determining whether a hypotensive condition has coincided with a transient condition of electrocardioactivity. If this approximation of systolic pressure was below a predetermined minimum value, as a result of the arrhythmia, a diastolic measurement would not be indicated in the data.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. An ambulatory patient monitoring system including a carrying pouch coupled to a patient, comprising:
   a. first portable monitoring means for independently measuring and storing a predetermined first diagnostic parameter of a first patient, said first portable monitoring means including; (1) a first power supply, (2) first control means coupled to said power supply for controlling said independent measurement and storage of said first diagnostic parameter, (3) means for sensing said first diagnostic parameter having an output coupled to said first control means, (4) first optical interface means coupled to said first control means for providing for digital communication external thereto, and (5) first memory means coupled to said first control means for storing a multiplicity of measurements of said first diagnostic parameter;
   b. at least a second portable monitoring means for measuring and storing a predetermined second diagnostic parameter, said second diagnostic parameter being a different physiological parameter than said first diagnostic parameter, said second portable monitoring means including; (1) a second power supply, (2) second control means coupled to said second power supply for generating a first control signal to initiate said measurement of said second diagnostic parameter, (3) means for sensing said second diagnostic parameter having an output coupled to said second control means, (4) second memory means coupled to said second control means for storing a multiplicity of measurements of said second diagnostic parameter, and (5) second optical interface means coupled to said second control means for digital communication with at least said first monitoring means, said first control signal being generated by said second control means at one of a plurality of predetermined variable repetition rates, said variable repetition rates being actuated by said second control means for predetermined time intervals, said second monitoring means being (1) operable independent of said first monitoring means for measuring said second diagnostic parameter of a second patient, and (2) positionable within said carrying pouch with said second optical interface in optical alignment with said first optical interface of said first monitoring means for measuring said second diagnostic parameter of said first patient responsive to both said first control signal and a second control signal generated by said first control means of said first monitoring means, said second control signal being transmitted by said first optical interface means to said second optical interface means responsive to a predetermined characteristic of said first diagnostic parameter being identified by said first control means; and
   c. computing means selectively couplable to both said first and second monitoring means for transferring data there between and selectively displaying said first and second diagnostic parameters, said computing means including at least a pair of serial interface ports, said computing means including means for input of (1) said variable repetition rates and said time intervals for transfer to said second control means, and (2) said first diagnostic parameter characteristic to said first control means.

2. The ambulatory patient monitoring system as recited in claim 1 where said computing means includes third optical interface means for selectable coupling with either said first or second monitoring means for transmitting data therebetween.

3. The ambulatory patient monitoring system as recited in claim 2 where said third optical interface means provides means for selectively transmitting either real time or stored diagnostic parameter information from a respective one of said first or second monitoring means.

4. The ambulatory patient monitoring system as recited in claim 1 where said first monitoring means includes means for detecting said second monitoring means being operative and disposed adjacent thereto.

5. The ambulatory patient monitoring system as recited in claim 1 where said first memory means is formed by a plurality of electrically erasable, electrically programmable, nonvolatile semiconductor memory devices.

6. The ambulatory patient monitoring system as recited in claim 1 where said first control means includes:
   a. first serial interface means for said selected coupling with one of said pair of serial interface ports of said computing means;
   b. first microprocessor means coupled to (1) said first serial interface means, (2) said first optical interface means, and (3) said first memory means for transmission of digital data therebetween; and,
   c. signal conditioning means coupled to said microprocessor means for amplifying, filtering and converting analog input signals to digital signals, said microprocessor means analyzing said digital signals to identify and categorize any of said digital signals representing any of a plurality of abnormal conditions.

7. The ambulatory patient monitoring system as recited in claim 6 where said second control signal is generated by said first microprocessor means responsive to (1) identifying a predetermined abnormality in said electrocardiographic signal, and (2) detection of said second monitoring means being operative and positionally located adjacent said first monitoring means for triggering a measurement by said second monitoring means.

8. The ambulatory patient monitoring system as recited in claim 6 where said first microprocessor means transmits an R-wave gate signal to said second monitoring means through said first optical interface means.

9. The ambulatory patient monitoring system as recited in claim 6 where said means for sensing said first diagnostic parameter includes a plurality of electrodes coupled to said signal conditioning means and being affixable to said first patient for conducting electrocardiographic signals therefrom.

10. The ambulatory patient monitoring system as recited in claim 9 where said second monitoring means includes an air pump fluidly coupled to an inflatable cuff affixable to a patient for inflation of said cuff responsive to either of said first or second control signals.

11. The ambulatory patient monitoring system as recited in claim 10 where said means for sensing said second diagnostic parameter includes (1) an audio transducer affixable to said patient, and (2) a pressure transducer fluidly coupled to said inflatable cuff.

12. The ambulatory patient monitoring system as recited in claim 11 where said second monitoring means further includes second microprocessor means coupled to both said audio and pressure transducers and said air pump for determining a blood pressure measurement, said second microprocessor means being further coupled to said second memory means for storing blood pressure measurement values therein.

13. The ambulatory patient monitoring system as recited in claim 12 where said microprocessor means determines said blood pressure measurement by (1) an auscultatory method using input signal from both said audio transducer and said pressure transducer when K sounds are present, and (2) an oscillometric method using input signals from said pressure transducer when K sounds are not detected.

14. The ambulatory patient monitoring system as recited in claim 1 where said second monitoring means includes second serial interface means for selective coupling with one of said pair of serial interface ports of said computing means for (1) reading data stored in said second memory means, (2) erasing said second memory means, (3) transmitting a replacement control algorithm to said second monitoring means, (4) entering patient identification data, and (5) entering measurement protocols.

15. An ambulatory patient monitoring system for measuring and storing a plurality of diagnostic parameter values, comprising:
a portable power supply:
microprocessor means coupled to said portable power supply for determining said diagnostic parameter values;
nonvolatile memory means coupled to said microprocessor means for storing both said plurality of diagnostic parameter values and a control algorithm, said nonvolatile memory being formed by a plurality of electrically programmable, electrically erasable semiconductor memory devices, said memory devices being all substantially simultaneously electrically erasable;
random access memory means coupled to said microprocessor means for temporary storage of said control algorithm, said microprocessor means transferring said control algorithm (1) from said nonvolatile memory means to said random access memory means preceding electrical erasure of said nonvolatile memory means, and (2) back to said nonvolatile memory means subsequent to said erasure thereof; and, sensor means coupled to said microprocessor means for providing measurement data thereto, said microprocessor means calculating said diagnostic parameter values from said measurement data.

16. The ambulatory patient monitoring system as recited in claim 15 further comprising:
means for supplying fluid to an inflatable cuff affixable to a patient coupled to said microprocessor means, said fluid supply means being actuated responsive to an inflate command control signal from said microprocessor means; and,
means for deflating said inflatable cuff coupled to said microprocessor means, said deflating means being responsive to a deflate command signal from said microprocessor means.

17. An ambulatory patient monitoring system for measuring and storing a plurality of diagnostic parameter values powered by a portable power source, comprising:
microprocessor means coupled to said portable power source for determining said diagnostic parameter values;
memory means coupled to said microprocessor means for storing said plurality of diagnostic parameter values;
means for stopping and starting operation of said microprocessor means to thereby conserve power from said portable power source; and,
sensor means coupled to said microprocessor means for providing measurement data thereto, said microprocessor means calculating said diagnostic parameter values from said measurement data.

18. The ambulatory patient monitoring system as recited in claim 17 further comprising:
means for supplying fluid to a inflatable cuff affixable to a patient, said fluid supply means being coupled to said microprocessor means and being actuated responsive to an inflate command control signal from said microprocessor means; and,
means for deflating said inflatable cuff coupled to said microprocessor means, said deflating means being responsive to a deflate command signal from said microprocessor means.

19. The ambulatory patient monitoring system as recited in claim 18 where said diagnostic parameter values are blood pressure values and said microprocessor means includes means for selectably calculating said blood pressure values by (1) an auscultatory method, and (2) an oscillometric method.

20. The ambulatory patient monitoring system as recited in claim 19 where said sensor means includes (1) an audio transducer affixable to said patient, and (2) a pressure transducer fluidly coupled to said inflatable cuff.

21. The ambulatory patient monitoring system as recited in claim 19 further comprising an optical interface coupled to said microprocessor means for receiving a gating signal optically transmitted from an external monitoring unit.

22. The ambulatory patient monitoring system as recited in claim 21 where said external monitoring unit is an ECG monitoring unit and said gating signal indicates the occurrence of an R-wave, thereby improving the accuracy of said blood pressure measurement methods.

23. The ambulatory patient monitoring system as recited in claim 17 where said stopping and starting means includes clock means for generating a periodic interrupt signal to restart said microprocessor means.

24. An ambulatory patient monitoring system, comprising:
  at least two monitoring units releasably secured to a patient for measuring different diagnostic parameters, each of said monitoring units comprising:
   a. a portable power source;
   b. microprocessor means coupled to said portable power source for controlling the measurement and storage of predetermined diagnostic parameters;
   c. memory means coupled to said microprocessor means for storing said predetermined diagnostic parameters;
   d. optical interface means coupled to said microprocessor means for communicating with another of said monitoring unit, said optical interface of a first of said at least two monitoring units optically transmitting a control signal representing detection of a predetermined characteristic of a first diagnostic parameter measured by said first monitoring unit to a second of said at least two monitoring units, said control signal being received by said optical interface of said second monitoring unit for initiating a measurement by said second monitoring unit of a second diagnostic parameter;
   e. signal conditioning means coupled to said microprocessor means for providing said diagnostic parameters thereto; and,
   f. input means coupled to a patient for sensing diagnostic parameters therefrom, said input means having an output coupled to said signal conditioning means.

* * * * *